United States Patent
Moulton et al.

(10) Patent No.: US 6,207,039 B1
(45) Date of Patent: Mar. 27, 2001

(54) PROCESS FOR RECOVERING ONIUM HYDROXIDES OR ONIUM SALTS FROM SOLUTIONS CONTAINING ONIUM COMPOUNDS USING ELECTROCHEMICAL ION EXCHANGE

(75) Inventors: Roger D. Moulton; David R. Hulme, both of Austin, TX (US)

(73) Assignee: Sachem, Inc., Austin, TX (US)

(*) Notice: Subject to any disclaimer, the term of this patent is extended or adjusted under 35 U.S.C. 154(b) by 0 days.

(21) Appl. No.: 09/277,560

(22) Filed: Mar. 26, 1999

Related U.S. Application Data
(60) Provisional application No. 60/080,978, filed on Apr. 7, 1998.

(51) Int. Cl.[7] .................................................... C02F 1/461
(52) U.S. Cl. ...................... 205/703; 204/524; 204/533
(58) Field of Search ........................... 205/703, 688; 204/524, 530, 533, 534, 536, 537, 541

(56) References Cited

U.S. PATENT DOCUMENTS

| | | | |
|---|---|---|---|
| 4,484,989 | * 11/1984 | Mansell ............................... | 204/59 R |
| 5,679,229 | 10/1997 | Goldstein et al. .................... | 204/524 |
| 5,753,097 | 5/1998 | Sharifian et al. ..................... | 205/437 |
| 5,833,832 | 11/1998 | Shay et al. ........................... | 205/413 |
| 5,853,555 | 12/1998 | Sharifian et al. ..................... | 204/537 |
| 5,858,191 | * 1/1999 | DiMascio et al. ..................... | 204/524 |
| 5,868,916 | 2/1999 | Moulton ............................... | 204/541 |
| 5,910,237 | * 6/1999 | Moulton et al. ..................... | 204/541 |
| 5,951,845 | * 9/1999 | Moulton ............................... | 205/746 |
| 5,968,338 | * 10/1999 | Hulme et al. ........................ | 205/703 |

OTHER PUBLICATIONS

International Search Report mailed Jul. 1, 1999 for PCT Patent Application Serial No. PCT/US99/07672.

* cited by examiner

*Primary Examiner*—Kathryn Gorgos
*Assistant Examiner*—Thomas H Parsons
(74) *Attorney, Agent, or Firm*—Renner, Otto, Boisselle & Sklar (57) ABSTRACT

In one embodiment, the present invention relates to a process for recovering one of an onium hydroxide and onium salt from a solution containing an onium compound involving the steps of charging the solution containing the onium compound to an electrochemical cell comprising at least two compartments, a cathode, an anode, and a divider, wherein at least one compartment comprises an ion exchange material; passing a current through the electrochemical cell whereby the onium hydroxide or the onium salt is produced; and recovering the onium hydroxide or the onium salt from the electrochemical cell.

38 Claims, 5 Drawing Sheets

PROCESS FOR RECOVERING ONIUM HYDROXIDES OR ONIUM SALTS FROM SOLUTIONS CONTAINING ONIUM COMPOUNDS USING ELECTROCHEMICAL ION EXCHANGE

This application claims benefit to provisional application Ser. No. 06/080,978, filed Apr. 7, 1998.

BACKGROUND OF THE INVENTION

1. Field of the Invention

This invention relates to processes for recovering onium hydroxides or onium salts from solutions containing onium compounds using electrochemical ion exchange techniques. In particular, the invention relates to processes for recovering one of onium hydroxides and onium salts from solutions containing onium hydroxides and/or onium salts using an electrochemical cell including at least one compartment containing an ion exchange material.

2. Description of the Related Art

Onium hydroxides, such as quaternary ammonium hydroxides including tetramethylammonium hydroxide (TMAH) and tetraethylammonium hydroxide (TEAH), are strong organic bases that have been known for many years. Quaternary ammonium hydroxides have found a variety of uses including use in zeolite manufacture and polymer manufacture. Aqueous solutions of quaternary ammonium hydroxides, particularly TMAH solutions, have also been used extensively as a developer for photoresists in printed circuit board and microelectronic chip fabrication. For a variety of reasons, it is desirable to minimize the overall amount of developer used in printed circuit board and microelectronic chip fabrication. One way to minimize the overall amount of hydroxide developer is to reuse the waste developer. Reusing developer reduces the amount lost and decreases disposal problems.

Waste developer contains impurities including ionic impurities and nonionic impurities. Ionic impurities include various metal cations such as sodium, potassium, zinc, nickel, aluminum, copper and calcium; and anions such as halides, nitrates, nitrites, carbonates, carboxylates, sulfates. Nonionic impurities include photoresists, surfactants, amines and numerous other organic molecules. Waste developer also contains relatively low concentrations of the hydroxide developer. Accordingly, there remains a continuing need to effectively recover hydroxide developer in a useable form so that it may be reused thereby minimizing the overall amount of developer used in printed circuit board and microelectronic chip fabrication.

U.S. Pat. No. 4,714,530 (Hale et al) describes an electrolytic process for preparing high purity quaternary ammonium hydroxides which utilizes a cell containing a catholyte compartment and an anolyte compartment separated by a cation-exchange membrane. The process comprises charging an aqueous solution of a quaternary ammonium hydroxide to the anolyte compartment, adding water to the catholyte compartment, and passing a direct current through the electrolysis cell to produce a higher purity quaternary ammonium hydroxide in the catholyte compartment which is subsequently recovered. The '530 patent also describes an improvement which comprises heating the quaternary ammonium hydroxide at an elevated temperature prior to charging the hydroxide to the anolyte compartment of the electrolytic cell.

U.S. Pat. No. 4,938,854 (Sharifian et al) also describes an electrolytic process for purifying quaternary ammonium hydroxides by lowering the latent halide content. The electrolytic cell may be divided into an anolyte compartment and a catholyte compartment by a divider which may be an anion or cation selective membrane. The cathode in the catholyte compartment comprises zinc, cadmium, tin, lead, copper or titanium, or alloys thereof, mercury or mercury amalgam.

Japanese Kokai Patent No. 60-131985 (1985) (Takahashi et al) describes a method of manufacturing a high purity quaternary ammonium hydroxide in an electrolysis cell which is divided into an anode chamber and a cathode chamber by a cation exchange membrane. A quaternary ammonium hydroxide solution containing impurities is charged to the anode chamber and a direct current is supplied between two electrodes after water has been charged to the cathode chamber. Purified quaternary ammonium hydroxide is obtained from the cathode chamber. The purified quaternary ammonium hydroxide contains reduced amounts of alkali metals, alkaline earth metals, anions, etc.

U.S. Pat. Nos. 5,439,564 and 5,545,309 (Shimizu et al) relate to methods of processing waste liquid containing an organic quaternary ammonium hydroxide by contacting the waste liquid with a cation-exchanging material, eluting organic quaternary ammonium cations from the cation-exchanging material, and electrolyzing the eluate in a two chamber electrolytic cell equipped with an anode, cathode and cation-exchanging membrane. Organic quaternary ammonium hydroxide is obtained from the cathode chamber of the electrolytic cell.

SUMMARY OF THE INVENTION

In one embodiment, the present invention relates to a process for recovering one of an onium hydroxide and an onium salt from a solution containing an onium compound involving the steps of charging the solution containing the onium compound to an electrochemical cell comprising at least two compartments, a cathode, an anode, and a divider, wherein at least one compartment comprises an ion exchange material; passing a current through the electrochemical cell whereby the onium hydroxide or the onium salt is produced; and recovering the onium hydroxide or the onium salt from the electrochemical cell.

In another embodiment, the present invention relates to a process for recovering one of an onium hydroxide and an onium salt from a solution containing an onium compound involving the steps of charging the solution containing the onium compound to an electrochemical cell comprising at least two compartments, a cathode, an anode, and a cation selective membrane, wherein at least one compartment comprises a cation exchange material; passing a current through the electrochemical cell whereby the onium hydroxide or the onium salt is produced; and recovering the onium hydroxide or the onium salt from the electrochemical cell.

In yet another embodiment, the present invention relates to a process for recovering a quaternary ammonium hydroxide from a solution containing a quaternary ammonium compound involving the steps of charging the solution containing the quaternary ammonium compound to an electrochemical cell comprising at least two compartments, a cathode, an anode, and a cation selective membrane, wherein at least one compartment comprises an ion exchange material; passing a current through the electrochemical cell whereby the quaternary ammonium hydroxide is regenerated; and recovering the quaternary ammonium hydroxide from the electrochemical cell.

As a result of the processes of the claimed invention, solutions of onium hydroxides can be obtained in which the concentration and purity is increased. Recycling spent solutions of onium hydroxides provides not only cost savings, but also environmental benefits by eliminating the need for synthesizing new hydroxide compound solutions and associated expensive purification processes and reducing the toxicity of waste solution effluents. An increased amount of water can be recovered after onium hydroxides are removed from solution. The relatively high concentration and purity of onium hydroxide solutions obtainable via the present invention can effectively be used in numerous applications where onium hydroxide solutions are required. Also as a result of the processes of the claimed invention, solutions of onium salts can be obtained in which the concentration and purity is increased.

DESCRIPTION OF THE PREFERRED EMBODIMENTS

In accordance with one embodiment of the present invention, onium hydroxides are recovered (that is, produced, purified, regenerated or recycled) from solutions containing an onium hydroxide and/or onium salt. In accordance with another embodiment of the present invention, onium salts are recovered (that is, produced, purified, regenerated or recycled) from solutions containing an onium hydroxide and/or onium salt. As used herein, an onium compound is a any compound containing an onium cation, such as at least one of an onium hydroxide and an onium salt.

In one embodiment, the solution containing an onium compound is a waste developer solution of an onium hydroxide after it has been used in a process, especially in developing processes associated with printed circuit board and microelectronic chip fabrication. As a result of such processes, impurities enter and contaminate the developer solution. In other words, the solution containing an onium compound may be a spent waste solution of an onium hydroxide. In another embodiment, the solution containing an onium compound is a waste solution of an onium salt after it has been used in a process. The solution or waste developer solution may contain other compounds, such as the impurities described above and below and/or an onium salt corresponding to an onium hydroxide. In yet another embodiment, the solution containing an onium compound is a solution of an first onium salt, and a second onium salt is recovered using the present invention.

The solutions containing onium compounds which are treated in accordance with the process of the present invention are mixtures, preferably solutions, containing an oxidizable liquid and from about 0.01% to about 50% by weight of the onium compound and generally will contain varying amounts of one or more undesirable impurities, for example, anions such as halide, carbonate, formate, nitrite, nitrate, sulfate, etc., some cations such as metals including zinc, aluminum, titanium, calcium, sodium, potassium and some neutral species such as photoresists, methanol, various amines, etc. The oxidizable liquid may be water, mixtures of water and an organic liquid, or an organic liquid. Organic liquids include alcohols and especially lower alcohols (from 1 to about 4 carbon atoms), such as methanol, ethanol, propanol, etc., glycols and the like.

In one embodiment, the process of the present invention is effective in reducing the amount of both ionic and nonionic impurities present in solutions of onium compounds, such as a solution of a quaternary ammonium hydroxide, while yielding onium hydroxides or onium salts of high purity. In a further embodiment, the process of the present invention results in a reduction of metal ion impurities as well as organic impurities in a solution of an onium compound, such as a quaternary ammonium hydroxide, while yielding onium hydroxides or onium salts of high purity. In another embodiment, the process of the present invention is useful in preparing purified onium hydroxides or onium salts, such as quaternary ammonium hydroxides, quaternary phosphonium hydroxides, tertiary sulfonium hydroxides, quaternary ammonium salts, quaternary phosphonium salts, and tertiary sulfonium salts.

The onium hydroxides may generally be characterized by Formula (I):

wherein A is an onium group and x is an integer equal to the valence of A. Examples of onium groups include ammonium groups, phosphonium groups, and sulfonium groups. In one embodiment, the onium hydroxide should be sufficiently soluble in a solution such as water, alcohol or other organic liquid, or mixtures thereof to permit a useful recovery rate.

The quaternary ammonium hydroxides and quaternary phosphonium hydroxides may be characterized by Formula (II):

(II)

wherein A is a nitrogen or phosphorus atom, $R^1$, $R^2$, $R^3$ and $R^4$ are each independently alkyl groups containing from 1 to about 20 carbon atoms, hydroxy alkyl or alkoxy alkyl groups containing from 2 to about 20 carbon Glatoms, aryl groups, or hydroxy aryl groups, or $R^1$ and $R^2$ together with A may form a heterocyclic group provided that if the heterocyclic group contains a C=A group, $R^3$ is the second bond.

The alkyl groups $R^1$ to $R^4$ may be linear or branched, and specific examples of alkyl groups containing from 1 to 20 carbon atoms include methyl, ethyl, propyl, butyl, pentyl, hexyl, heptyl, octyl, isooctyl, nonyl, decyl, isodecyl, dodecyl, tridecyl, isotridecyl, hexadecyl and octadecyl groups. $R^1$, $R^2$, $R^3$ and $R^4$ also may be hydroxyalkyl groups such as hydroxyethyl and the various isomers of hydroxypropyl, hydroxybutyl, hydroxypentyl, etc. In one preferred embodiment, $R^1$, $R^2$, $R^3$ and $R^4$ are independently alkyl groups containing one to ten carbon atoms and hydroxyalkyl groups containing from two to three carbon atoms. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

The quaternary ammonium hydroxides which can be recycled or purified in accordance with the process of the present invention may be represented by Formula (III):

(III)

wherein $R^1$, $R^2$, $R^3$ and $R^4$ are as defined in Formula II. In one preferred embodiment, $R^1$ to $R^4$ are alkyl groups containing from 1 to about 4 carbon atoms and hydroxyalkyl groups containing 2 or 3 carbon atoms. Most often the quaternary ammonium hydroxides purified in accordance with the process of the invention will be tetramethylammonium hydroxide (TMAH) or tetraethylammonium hydroxide (TEAH). Specific examples of such ammonium hydroxides include tetramethylammonium hydroxide, tetraethylammonium hydroxide, tetrapropylammonium hydroxide, tetrabutylammonium hydroxide, tetra-n-octylammonium hydroxide, methyltriethylammonium hydroxide, diethyldimethylammonium hydroxide, methyltripropylammonium hydroxide, methyltributylammonium hydroxide, cetyltrimethylammonium hydroxide, trimethylhydroxyethylammonium hydroxide, trimethylmethoxyethylammonium hydroxide, dimethyidihydroxyethylammonium hydroxide, methyltrihydroxyethylammonium hydroxide, phenyltrimethylammonium hydroxide, phenyltriethylammonium hydroxide, benzyltrimethylammonium hydroxide, benzyltriethylammonium hydroxide, dimethylpyrolidinium hydroxide, dimethylpiperidinium hydroxide, diisopropylimidazolinium hydroxide, N-alkylpyridinium hydroxide, etc.

Examples of quaternary phosphonium hydroxides representative of Formula (II) wherein A=P which can be purified in accordance with the process of the present invention include tetramethylphosphonium hydroxide, tetraethylphosphonium hydroxide, tetrapropylphosphonium hydroxide, tetrabutylphosphonium hydroxide, methyltributylphosphonium hydroxide, trimethylhydroxyethylphosphonium hydroxide, dimethyldihydroxy-ethylphosphonium hydroxide, methyltrihydroxyethylphosphonium hydroxide, phenyltrimethylphosphonium hydroxide, phenyltriethylphosphonium hydroxide and benzyltrimethylphosphonium hydroxide, etc.

In another embodiment, the tertiary sulfonium hydroxides which can be regenerated, produced, recycled or purified in accordance with this invention may be represented by Formula (IV):

(IV)

wherein $R^1$, $R^2$ and $R^3$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R^1$ and $R^2$ together with S may form a heterocyclic group provided that if the heterocyclic group contains a C=S group, $R^3$ is the second bond.

Examples of the tertiary sulfonium hydroxides represented by Formula (IV) include trimethylsulfonium hydroxide, triethylsulfonium hydroxide, tripropylsulfonium hydroxide, etc.

Onium hydroxides are commercially available. Additionally, onium hydroxides can be prepared from the corresponding onium salts such as the corresponding onium halides, carbonates, formates, sulfates and the like. Various methods of preparation are described in U.S. Pat. Nos. 4,917,781 (Sharifian et al) and 5,286,354 (Bard et al) which are hereby incorporated by reference. There is no particular limit as to how the onium hydroxide is obtained or prepared.

The onium salts which can be recovered, regenerated, produced, recycled or purified in accordance with this invention are represented by a combination of any of the onium cations described above and a salt anion or acid anion. Referring to any one of Formulae (I) to (IV), an onium salt is represented when the OH⁻ anion is replaced with a salt or acid anion. Salt anions include formates, acetates, other organic acid anions, halides (fluorides, chlorides, bromides and iodides), bicarbonates and carbonates, nitrates, phosphates, sulfates and the like. Specific examples, which are not listed for the sake of brevity, include the corresponding formate, acetate, fluoride, chloride, bromide, iodide, bicarbonate, carbonate, nitrate, phosphate and sulfate salts of any of the specific examples of quaternary ammonium, quaternary phosphonium and tertiary sulfonium hydroxides listed above.

Prior to charging the solutions containing the onium hydroxide and/or onium salts and/or impurities to an electrochemical cell containing an ion exchange material, and/or after recovering the onium hydroxides or onium salts from the electrochemical cell containing an ion exchange material, the solutions may be optionally concentrated or otherwise pretreated and/or post-treated. That is, the concentration of the onium hydroxide and/or onium salt in the solution may be increased prior to incorporation into (and/or after recovery from) an electrochemical cell containing the ion exchange material and/or various impurities may be removed from the onium compound solution.

In some embodiments, it is preferable to concentrate the solution of the onium hydroxide and/or onium salt prior to incorporation into (and/or after recovery from) an electrochemical cell containing the ion exchange material. Concentration procedures are known to those skilled in the art and include evaporation, distillation, nanofiltration and reverse osmosis among others.

In other embodiments, it is preferable to pretreat (and/or post-treat) the solution of the onium compound with some form of filtration prior to incorporation into (and/or after recovery from) an electrochemical cell containing the ion exchange material in accordance with the invention. Various types of filtration can be performed including gravity filtration, microfiltration such as nanofiltration, ultrafiltration, cross-flow filtration, cartridge filtration, vacuum filtration and pressure induced filtration. Related straining and screening pretreatments and post-treatments may also be performed. Filter membranes can be made of known materials useful for separating solids from liquids including plastics such as PTFE, PVDF, PET, nylons, polyethylene and polypropylene, cellulose acetate, cellulose nitrate, regenerated cellulose, nitrocellulose, paper including ashless paper, various fibers including glass fibers, and various particulates including activated carbon, silica, sand, etc.

Alternatively, pretreatment and/or post-treatment can involve adsorption. Adsorption involves contacting the solution of the onium compound with various particulate materials, for example activated carbon and/or Ambersorb® available from Rohm & Haas, so that organic impurities are adsorbed and thus removed from solution by the particulate material.

In some embodiments, more than one type (or pass) of a filtration pretreatment and/or post-treatment can be performed as each filtration treatment may remove a different species of impurity. For example, in one embodiment two filtration treatments are performed: organic impurities are substantially or partially removed by gravity filtration and metal impurities are substantially or partially removed by another pass of gravity filtration after increasing the pH of the solution causing certain metals to form insoluble hydroxide salts thereby facilitating filtration (and thus separation of the insoluble species).

In other embodiments, it is preferable to pretreat and/or post-treat the solution of the onium compound with some form of metal treatment prior to incorporation into (and/or after recovery from) an electrochemical cell containing the ion exchange material in accordance with the invention. A metal treatment removes excess metal impurities from the solution of the onium compound. In one embodiment, metal treatment involves contacting a solution of the onium compound with a preliminary ion exchange material for metal removal. The preliminary ion exchange material is preferably a preliminary cation exchange material which can selectively discriminate between metal cations and onium cations so that at least a portion of metal ion impurities in the solution of the onium compound is adsorbed by the preliminary ion exchange material. For example, a preliminary ion exchange material, for which sodium has an affinity, can be used as a metal pretreatment to remove sodium from the solution of the onium compound.

In another embodiment, metal treatment involves contacting a solution of the onium compound with a metal complexing compound. Metal complexing compounds adsorb, bond to, complex, coordinate, chelate or otherwise engage at least a portion of the metal ion impurities in the solution of the onium compound thereby removing them from solution. Examples of metal complexing compounds include crown ethers, cryptands and chelating compounds (diamines, diketonates, etc) specifically including chelating resins.

In yet another embodiment, metal treatment involves precipitation and/or co-precipitation. Precipitation and/or co-precipitation involve contacting a solution of the onium compound with an acid or salt capable of forming an insoluble precipitate (at least partially insoluble) with a metal cation thereby enabling easy removal of the precipitate and thus the metal from solution prior to incorporation into (and/or recovery from) an electrochemical cell containing the ion exchange material in accordance with the invention.

In still yet another embodiment, pre- or post-treatment involves chemical oxidation and/or electrochemical oxidation. Chemical oxidation and electrochemical oxidation involve contacting a solution of the onium compound with an oxidizing compound thereby enabling easy removal of the oxidized compound and thus the target impurity from solution prior to incorporation into (and/or recovery from) an electrochemical cell containing the ion exchange material in accordance with the invention.

In still yet another embodiment, pre- or post-treatment involves neutralization. Neutralization involves contacting a solution of the onium compound with a pH neutralizer, and often involves a filtration step.

In accordance with the process of the present invention, one of an onium hydroxide and onium salt such as those described above is recovered (that is, produced, purified, regenerated or recycled) in a process involving an electrochemical cell containing an ion exchange material. The ion exchange material is generally contained in the feed compartment of the electrochemical cell, but it may also be contained in other compartments as well. The electrochemical cell may involve electrolysis in an electrolytic cell or electrodialysis in an electrodialytic cell. The electrochemical cells, generally speaking, contain at least an anode, a cathode, a divider, and an ion exchange material.

A number of electrolytic and electrodialytic cells containing various unit cells and multiple unit cells are described herein which are useful in the process of the present invention. Multiple unit cells may be defined by a number of compartments between an anode and a cathode, or multiple unit cells may be defined by a number of compartments including an anode and cathode. Multiple unit cells including an anode and cathode may take a monopolar configuration, or a bipolar configuration. There is no particular limit to the number of unit cells which can be used. Nevertheless, in one embodiment, electrochemical cells which are used according to the present invention contain from 1 to about 25 unit cells, and preferably from 1 to about 10 unit cells.

The unit cells may contain at least either two or three compartments defined by the anode, cathode, at least one divider which is at least one of an anion selective membrane, a cation selective membrane, a bipolar membrane and a nonionic membrane which may act as microporous diffusion barriers, filters, or have controlled pore size or pore size distribution allowing or not allowing certain ions to pass therethrough, and at least one of the compartments contains an ion exchange material. The various ion exchange materials, anion selective membranes, cation selective membranes, bipolar membranes and nonionic membranes useful in the electrochemical cells used in the invention are described more fully below.

Electrochemical cells according to the present invention contain at least either two compartments or three compartments, wherein at least one of the compartments contains an ion exchange material. Electrochemical cells containing at least two compartments generally have a feed compartment and a recovery compartment. Electrochemical cells containing at least three compartments generally have a feed compartment, a recovery compartment and at least one of an acid compartment, a pass compartment and a buffer compartment. In certain embodiments, an electrochemical cell according to the present invention may have two or more of each of the compartments described above. In other embodiments, the electrochemical cell may have two or more of one or more of the compartments listed above. For example, in one embodiment, an electrochemical cell may have a feed compartment, two buffer compartments and a recovery compartment.

A solution is charged to each compartment. The solution may be aqueous based, alcohol or glycol based, another organic solution or combinations thereof. In other words, the solutions may contain water, mixtures of water and an organic liquid, or an organic liquid, where the organic liquids include alcohols, such as methanol and ethanol, glycols and the like. In a preferred embodiment, the solution charged into each compartment is an aqueous solution or an alcohol based solution.

The solution charged into the feed compartment contains the onium compound and typically impurities. The concentration of the onium compound initially charged into the feed compartment is in the range from about 0.001 M to about 6 M. In another embodiment, the concentration of the onium compound in the solution charged into the feed compartment is from about 0.01 M to about 3 M. In a preferred embodiment, the concentration of the onium compound in the solution charged into the feed compartment is from about 0.1 M to about 1.5 M. In electrochemical cells containing two or more feed compartments, the concentrations of the onium compounds in the solutions charged into the feed compartments may be the same or different for each feed compartment. The feed compartment, as the term implies, initially holds the onium compound solution. The feed compartment typically contains an ion exchange material.

The recovery compartment initially is charged with a solution and preferably an aqueous solution. The solution charged to the recovery compartment may or may not contain an ionic compound. An ionic compound is a chemical compound that partially or completely ionizes in solution, such as an electrolyte. Examples of ionic compounds include salts, metal salts and acids or any compound which forms an anion and cation when placed in water. In a preferred embodiment where onium hydroxides are recovered, the ionic compound is an onium hydroxide corresponding to the onium compound charged into the feed compartment (or the same as the onium hydroxide eventually recovered from the recovery compartment). In another preferred embodiment where onium salts are recovered, the ionic compound is an acid containing an anion of the onium salt recovered from the feed compartment. In yet another embodiment, the ionic compound is different from the onium compound charged into the feed compartment. After passing a current through the electrochemical cell, one of an onium hydroxide or onium salt may be recovered or otherwise obtained from the recovery compartment at a certain concentration. In one embodiment, the concentration of the onium hydroxide or onium salt in the recovery compartment is above about 0.5 M. In another embodiment, the concentration of the onium hydroxide or onium salt in the recovery compartment is above about 1 M. In yet another embodiment, the concentration of the onium hydroxide or onium salt in the recovery compartment is above about 2 M. In electrochemical cells containing two or more recovery compartments, the concentrations of the organic hydroxide or onium salt in the solutions recovered from the recovery compartments may be the same or different for each recovery compartment.

The buffer compartment, if present, contains a solution of an ionic compound at a certain concentration. The buffer compartment containing an ionic compound serves to maintain conductivity and enable lower operating cell voltages. The concentration of the ionic compound in the solution charged into the buffer compartment is in the range from about 0.1 M to about 5 M. In a preferred embodiment, the concentration is from about 0.5 M to about 2 M. And in a most preferred embodiment, the concentration is from about 0.7 M to about 1.5 M. In electrochemical cells containing two or more buffer compartments, the concentrations of the ionic compound in the solutions charged into the buffer compartments may be the same or different for each buffer compartment.

The pass compartment, if present, initially is charged with a solution and preferably an aqueous solution. The solution charged to the pass compartment may or may not contain an ionic compound. The ionic compound, if present, may be the same or different from the ionic compound of the buffer compartment. In most embodiments, the pass compartment is defined by two cation exchange membranes. After passing a current through the electrochemical cell, the onium cation passes through the pass compartment in embodiments where a pass compartment is used. Since most undesirable impurities do not pass through the pass compartment, the pass compartment serves to further purify the resultant onium hydroxide.

The acid compartment is charged with a solution and preferably an aqueous solution. The solution charged to the acid compartment may or may not contain an ionic compound. The ionic compound, if present, may be the same or different from the ionic compound of the buffer compartment. The concentration of the ionic compound in the solution charged into the acid compartment is in the range from about 0.1 M to about 6 M. In a preferred embodiment, the concentration is from about 0.2 M to about 3 M. And in a most preferred embodiment, the concentration is from about 0.5 M to about 1.5 M. After passing a current through the electrochemical cell, the onium cation migrates toward the cathode while onium salt anions pass from the feed compartment to the acid compartment, if present. Where appropriate, an acid may be recovered from the acid compartment, especially in a continuous operation.

Operation of the process of the present invention may be continuous or batchwise. Operation of the process of the present invention generally is continuous and certain components are continuously recirculated. Circulation is effected by pumping and/or by gas evolution.

According to the present invention, a solution containing an onium compound is charged to a feed compartment with an ion exchange material so that the ion exchange material adsorbs at least one of onium cations (cations derived from onium hydroxide and/or onium salt), non-onium cations, onium salt anions (anions derived from an onium salt) and/or non-onium salt anions. In a preferred embodiment, the ion exchange material is a cation exchange material. The cation exchange material may be a weakly acidic cation exchange material, an intermediately acidic cation exchange material, a strongly acidic cation exchange material or combinations thereof. In another preferred embodiment, the ion exchange material is a mixed bed of an anion exchange material and a cation exchange material.

The ion exchange material may be in the form of anyone of a powder, pellets, granuoles, films and/or fibrous materials. Two or more ion exchange materials may be combined, for example, as a combination of a weakly acidic cation exchange material and a strongly acidic cation exchange material, a combination of an intermediately acidic cation exchange material and a strongly acidic cation exchange material, a combination of an anion exchange material and a cation exchange material, a combination of an inorganic cation exchange material and an organic cation exchange material, a combination of two or more cation exchange materials each in a different form, such as a powder and a fiber, depending upon the identity and properties of the onium compound solution. Given the handleability, economical aspects and ion-exchange capacity of the cation exchange materials, preferred are granular weakly acidic cation exchange resins, intermediately acidic cation exchange resins, anion exchange resins and/or strongly acidic cation exchange resins.

In one embodiment, examples of the ion exchange material include gelled or porously-shaped cation exchange resins produced by introducing sulfonic acid groups, carboxylic acid groups, phosphate groups (phosphoric and phosphorous acid groups) and chelating groups into a polymer or copolymer base of, for example, styrenic polymers or copolymers such as polystyrene and the like, acrylic polymers or copolymers such as polyacrylic resins and the like, methacrylic polymers and copolymers such as polymethacrylic resins and the like and tetrafluorethylenic polymers or copolymers such as polytetrafluoroethylene and the like, or into a modified polymer or copolymer base to be prepared by modifying the polymers or copolymers with a crosslinking agent such as divinylbenzene or the like. The cation exchange materials further include inorganic cation exchange materials such as zeolite, titanium phosphate, zirconium phosphate, polyantimonic acid, manganese dioxide, silica gel and the like.

In another embodiment, the ion exchange material includes selective cation exchange resins. Selective ion exchange resins discriminate between various cations based upon at least one of chelation, coordination, size, mobility, charge distribution and the like. For example, a selective ion or cation exchange resin may adsorb a metal cation, such as sodium, while permitting an onium cation, such as a quaternary ammonium cation, to pass therethrough. In a preferred embodiment, the selective cation exchange resin is a size selective cation exchange resin or a mobility selective cation exchange resin.

Specific preferred examples include cation exchange resins sold under the trade designations AMBERLITE® and DOWEX® from Rohm & Haas Co. and Dow Chemical Co., respectively. More specific examples include those under the trade designation AMBERLITE, such as IR-100, IR-105, IR-105 G, IR-112, IR-120, IR-122, IR-124, IRC-50, IRC-76, and IRC-84SP and under the trade designation DUOLITE, such as C-280, C-291, C-433 and C-464 from Rohm & Haas Co.; C-464 from Sumitomo Chemical Co.; those under the trade designation DOWEX, such as HGRW2, HCR-S, HGRW2, MWC-1, 50WX2, 50WX4, and 50WX8 and those under the trade designation MONOSPHERE DOWEX, such as C350, C500 and C650 from Dow Chemical Co.; Ionac CC and C-267 from Sybron; various cation exchange resins from Organo Co.; and those under the designation DIAION, such as PK21 6H, PK212, PK 228, HPK25, SK-1BS, SK-104, SK-1 12, SK-112, SK-116, WK20, WK40 and WK100 from Mitsubishi Kasei Corp. In a preferred embodiment, the cation exchange resin is at least one of IRC-84SP from Rohm & Haas Co.; MONOSPHERE DOWEX C350, C500 and C650 from Dow Chemical Co.; and PK21 6H, PK212 and WK40 from Mitsubishi Kasei Corp. Specific examples of chelating resins include those under the trade designation AMBERLITE, such as IR-718, those under the trade designation DUOLITE, such as C-467 and GT-73, and those under the designation DIAION, such as CR10, CR11 and CR20.

In another embodiment, examples of the ion exchange material include gelled or porously-shaped anion exchange resins produced by introducing quaternary ammonium groups or primary, secondary and tertiary amino groups into a polymer or copolymer base of, for example, styrenic polymers or copolymers such as polystyrene and the like, acrylic polymers or copolymers such as polyacrylic resins and the like, methacrylic polymers and copolymers such as polymethacrylic resins and the like and tetrafluorethylenic polymers or copolymers such as polytetrafluoroethylene and the like, or into a modified polymer or copolymer base to be prepared by modifying the polymers or copolymers with a crosslinking agent such as divinylbenzene or the like. Weak anion exchange resins and/or strong anion exchange resins may be employed.

Specific preferred examples include anion exchange resins sold under the trade designations AMBERLITE® and DOWEX® from Rohm & Haas Co. and Dow Chemical Co., respectively. More specific examples include those under the trade designation AMBERLITE, such as IRA-35, IRA-68, IRA-93, IRA-94, IRA-400, IRA-401, IRA-402, IRA-410, IRA-416, lRA-420, IRA-458, IRA-900, IRA-904, IRA-938 and IRA-958; those under the trade designation DOWEX, such as 1X2, 1X4, 1X8, 2X8, 11, MSA-1, MSA-2, SBR, 21K, SBR-P, SBR-P-C, 550, A, G-55, XUS, SAR, MWA-1, WBA, WGR-2 and A2 and those under the trade designation MONOSPHERE DOWEX from Dow Chemical Co.; under the trade designation DUOLITE, such as A-7, A-101, A-102, A-104, A-113, A-116, A-132, A-147, A-161, A-162, A-165, A-171, A-1 73, A-181, A-368, A-375 and A-378 from Rohm & Haas Co.; various cation exchange resins from Sumitomo Chemical Co., from Organo Co. and from Sybron; and those under the designation DIAION, such as HPA25, PA308, PA312, PA408, PA418, SA 10A, SA11A, SA 12A, SA10AS, SA20A, SA21 A, WA11, WA30 and WA103 from Mitsubishi Kasei Corp.

Mixed bed materials include any one or more of the above mentioned cation exchange resins in combination with any one or more of the above mentioned anion exchange resins. Specific examples of commercially available mixed bed resins include those under the trade designation AMBERLITE, such as MB-I and MB-3, those under the trade designation DUOLITE, such as MB5113 and MB6113, and those under the designation DOWEX, such as MR-3, MR-3C, MR-1 2 and 11 A8.

Specific examples of selective ion exchange resins discriminate between various cations based upon at least one of chelation, coordination, size, mobility, charge distribution and the like include resins including cyclic ether compounds include crown ethers such as 1 2-crown-4 (1,4,7,10-tetraoxacyclododecane); 15-crown-5 (1,4,7,10,13-pentaoxacyclopentadecane); 18-crown-6 (1 4,7,10,13,16-hexaoxacyclooctadecane); (12-crown-4)-2-methanol (2-(hydroxymethyl)-12-crown-4-); (+)-( 18-crown-6)-2,3, 11,1

2-tetracarboxylic acid, 4'-aminobenzo-15-crown-5; 4'-aminobenzo-18-crown-6; 2-(aminomethyl)-15-crown-5; 2-(aminomethyl)-18-crown-6; 4'-amino-5'-nitrobenzo-15-crown-5; 1-aza-12-crown-4; 1-aza-15-crown-5; 1-aza-18-crown-6; benzo-12-crown-4; benzo-15-crown-5; benzo-18-crown-6; bis[(benzo-15-crown-5)-15-ylmethyl] pimelate; 4'-bromobenzo-18-crown-6; dibenzo-18-crown-6; dibenzo-24-crown-8; dibenzo-30-crown-10; ar,ar'-di-tert-butyldibenzo-18-crown-6; dicyclohexano-18-crown-6; dicyclohexano-24-crown-8; 4'-formylbenzo-15 crown-5; 2-(hydroxymethyl)-1 2-crown-4; 2-(hydroxymethyl)-15-crown-5; 2-(hydroxymethyl)-18-crown-6;4'-nitrobenzo-15-crown-5; 4-vinylbenzo-18-crown-6; 1,8-dihydroxy-dibenzo-14-crown-4; 1,1 1-diol-20-crown-6; poly-[(dibenzo-18-crown-6)-coformaldehyde]; and bis[(1 2-crown-4)-2-methyl] 2-methyl-2-dodecylmalonate; and cyclic ether compounds which additionally contain nitrogen atoms in the ring structure, such as 2.2.2-cryptate and 2.2.1-cryptate (cryptands). Various examples of formulae, and methods of preparing cyclic ether compounds are described in U.S. Pat. No. 5,393,892 to Crakowiak et al, the relevant subject matter of which is hereby incorporated by reference.

The ion exchange material is contained in the feed compartment of the electrochemical cell. In some embodiments, other electrochemical cell compartments may contain an ion exchange material (two or more compartments of one electrochemical cell may contain an ion exchange material). The porousness of the ion exchange material selectively permits solvent and certain ions to migrate through the ion exchange material. The ion exchange material fills enough of a compartment of an electrochemical cell to facilitate the recovery of onium hydroxides using the methods of the present invention.

In one embodiment, the ion exchange material fills the entire compartment of an electrochemical cell (feed compartment). It is understood that since the ion exchange material is porous, filling the entire compartment does not mean assuming all of the space between two dividers or a divider and an electrode. In another embodiment, the ion exchange material fills at least about 50% (by volume) of the feed compartment of an electrochemical cell. In yet another embodiment, the ion exchange material fills at least about 25% of the feed compartment of an electrochemical cell. In still yet another embodiment, the ion exchange material fills at least about 10% of the feed compartment of an electrochemical cell. In another embodiment, the ion exchange material fills at least about 5% of the feed compartment of an electrochemical cell. In yet another embodiment, the ion exchange material fills at least about 1% of the feed compartment of an electrochemical cell.

Various materials can be used as anodes in the electrochemical cells. For example, the anode may be made of metals such as titanium-coated electrodes, tantalum, nickel, zirconium, hafnium or alloys of the same. Generally, the anodes will have a non-passivable and catalytic film which may comprise metallic noble metals such as platinum, iridium, rhodium or alloys thereof, or a mixture of electroconductive oxides containing at least one oxide or mixed oxides of a noble metal such as platinum, iridium, ruthenium, palladium or rhodium. In one embodiment, the anode is a dimensionally stable anode such as an anode having a titanium base with ruthenium and/or iridium oxides thereon. In a preferred embodiment, the anode is a dimensionally stable anode having a titanium base with ruthenium oxide thereon.

Various materials which have been used as cathodes in electrochemical cells can be included in the cells used in the above and other embodiments of the present invention. Cathode materials include nickel, iron, stainless steel, nickel plated titanium, graphite, carbon steel (iron) or alloys thereof etc. The term "alloy" is used in a broad sense and includes intimate mixtures of two or more metals as well as one metal coated onto another metal.

The electrochemical cell utilized in the process of the present invention contains at least one divider selected from nonionic and ionic selective membranes, and in some embodiments at least one bipolar membrane. Compartments are defined as the area between two of: nonionic membranes, ionic selective membranes and/or bipolar membranes and/or the anode(s) and/or the cathode(s). The nonionic membranes, ionic selective membranes and/or bipolar membranes function as diffusion barriers and/or gas separators. The nonionic membranes, ionic selective membranes, bipolar membranes, anodes and cathodes also function as a means of containing the ion exchange material.

The cation selective membranes used in the cells and the process of the invention may be any of those which have been used in the electrochemical purification or recycling of onium hydroxides and onium salts. Preferably, the cation exchange membranes should contain a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic and/perfluorocarboxylic acid, perfluorocarbon polymer membranes such as sold by the E.l. dupont Nemours & Co. under the general trade designation "Nafion" such as DuPont's Cationic Nafion 902 membrane. Other suitable cation selective membranes include CMV cation selective membranes from Asahi Glass and styrenedivinyl benzene copolymer membranes containing cation selective groups such as sulfonate groups, carboxylate groups, etc. Raipore Cationic R1010, (from Pall RAI), and NEOSEPTA CMH and NEO-SEPTA CM1 membranes from Tokuyama Soda are useful particularly with the higher molecular quaternary compounds. The preparation and structure of cation selective membranes are described in the chapter entitled "Membrane Technology" in Encyclopedia of Chemical Technology, Kirk-Othmer, Third Ed., Vol. 15, pp. 92–131, Wiley & Sons, New York, 1985. These pages are hereby incorporated by reference for their disclosure of various cation selective membranes which can be useful in the process of the present invention. The use of at least one cation selective membrane in the electrochemical cell is preferred. Size selective cation selective membranes may also be used as the cation selective membrane. Examples of the size selective cation selective membranes include CMS ion selective membrane from Tokuyama Soda and CSV ion selective membrane from Asahi Glass.

Any anion selective membrane may be utilized including membranes used in processes for the desalination of brackish water. Preferably, membranes should be selective with respect to the particular anions present in the cell (e.g., halide ions). The preparation and structure of anionic membranes are described in the chapter entitled "Membrane Technology" in Encyclopedia of Chemical Technology, Kirk-Othmer, Third Ed., Vol. 15, pp. 92–131, Wiley & Sons, New York, 1985. These pages are hereby incorporated by reference for their disclosure of various anionic membranes which may be useful in the process of the present invention.

Among the anion selective membranes which may be utilized in the electrochemical cell and which are commercially available are the following: AMFLON, Series 310, based on fluorinated polymer substituted with quaternary ammonium groups produced by American Machine and Foundry Company; IONAC MA 3148, MA 3236 and MA 3475, based on polymer substituted with quaternary ammonium derived from heterogenous polyvinylchloride produced by Ritter-Pfaulder Corp., Permutit Division; Tosflex IE-SF 34 or IE-SA 48 made by Tosoh Corp. which is a membrane designed to be stable in alkaline media; NEOSEPTA AMH, NEOSEPTA ACM, NEOSEPTA AFN or NEOSEPTA ACLE-SP from Tokuyama Soda Co.; and Selemion ASV, Selemion AMV and Selemion AAV from Asahi Glass. In one embodiment, the Tosflex IE-SF 34 and NEOSEPTA AMH anion exchange membranes are preferred because of their stability in alkaline solutions, such as the hydroxide containing solutions which are involved in the process of the invention.

The bipolar membranes used in the electrochemical cells are composite membranes containing three parts: a cation selective side or region, an anion selective side or region, and an interface between the two regions. When a direct current passes across a bipolar membrane, with the cation selective side toward or facing the cathode, electrical conduction is achieved by the transport of $H^+$ and $OH^-$ ions which are produced by the dissociation of water which occurs at the interface under the influence of an electrical field. Bipolar membranes are described, for example, in U.S. Pat. Nos. 2,829,095, 4,024,043 (single film bipolar membranes) and in 4,116,889 (cast bipolar membranes). The bipolar membranes useful in the process of the present invention include NEOSEPTA BIPOLAR 1 by Tokuyama Soda, WSI BIPOLAR, and Aqualytics Bipolar membranes.

The nonionic membranes used in the electrochemical cells include porous nonionic dividers and size selective membranes. Size selective membranes include nanoporous membranes. Specific examples of nonionic membranes include those under the trade designation Celgard from Hoechst Celanese. Examples of size selective membranes include MPF-34 nanofiltration membrane from Kiryat-Weizmann LTD., Desal-5 from LCI, Inc., and ESNA nanofiltration membrane from Hydronautics. Other nanofiltration membranes are available from Dow and FilmTec.

After the onium compound is charged to the feed compartment of an electrochemical cell containing an ion exchange material, a current (generally direct current) is applied between the anode(s) and the cathode(s). The current which is passed through the electrochemical cell is a current dictated by the design and performance characteristics of the cell, which are readily apparent to those skilled in the art and/or can be determined by routine experimentation. Current densities between about 10 and about 500 milliamps per square centimeter may be used, and current densities between about 70 and about 300 milliamps per square centimeter are preferred. Higher or lower current densities can be used for certain specific applications. The current density is applied to the cell for a period of time which is sufficient to result in the regeneration, formation or purification of the desired amount or concentration of the onium hydroxide in the recovery compartment.

In the electrochemical cell, it is generally desirable that the temperature of the liquids within the cell be maintained within the range of from about 2° C. to about 90° C., and preferably from about 20° C. to about 60° C. It is also generally desirable that the pH of the liquids within the cell is either alkaline or acidic. This can be accomplished by adding appropriate amounts of an acid or hydroxide compound to an appropriate compartment(s) of the electrochemical cell. Since the claimed process is a process involving hydroxide ions and/or acid ions, the pH of the cell and each compartment changes as the process is practiced, and in particular, the pH generally increases in the recovery compartment and decreases in the acid compartment, if present, as the process is practiced.

Several embodiments of electrochemical cells which may be used in the present invention will be described with reference to the figures. Although numerous embodiments of various electrochemical cells are described in the figures, it will be readily apparent to those skilled in the art that additional numerous embodiments not specifically described in the figures exist within the scope of the invention.

In general, in embodiments where an onium hydroxide is recovered from an electrochemical cell containing an ion exchange material, the electrochemical cell contains at least one divider which is a nonionic membrane and a cation selective membrane. In embodiments where an onium salt is recovered from an electrochemical cell containing an ion exchange material, the electrochemical cell contains at least one divider which is a cation selective membrane. In embodiments where an onium salt is recovered from an electrochemical cell, if the onium salt recovered is different from the onium salt in the onium compound solution charged to the feed compartment which contains an onium salt, the onium salt of the onium compound solution is a first onium salt while the onium salt recovered from the recovery compartment is a second onium salt (when the first and second onium salts are the same, a purification process is performed and when the first and second onium salts are different, a production or conversion process is performed).

Figure 1:
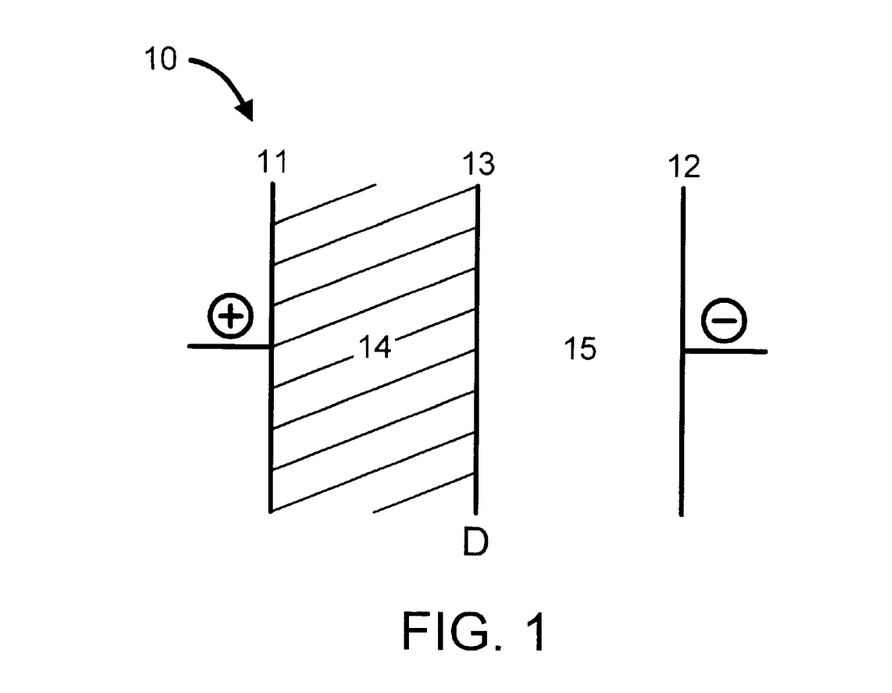
FIG. 1 is a schematic representation of a two compartment electrochemical cell containing one unit cell in accordance with the present invention.

An embodiment of an electrochemical cell is illustrated in FIG. 1, which is a schematic representation of an electrochemical cell 10 containing an anode 11, a cathode 12 and a divider 13, such as a nanoporous membrane. The electrochemical cell 10 contains two compartments; namely, a feed compartment 14 and a recovery compartment 15. The feed compartment 14 contains an ion exchange material.

In operation of the electrochemical cell 10 illustrated in FIG. 1, an onium compound solution is charged to the feed compartment 14. A solution, preferably an aqueous solution, of an ionic compound is charged to the recovery compartment 15. An electrical potential is established and maintained between the anode and the cathode to produce a flow of current across the cell whereupon the onium compound cation is attracted toward the cathode and passes through the ion exchange material and divider 13 into the recovery compartment 15. The onium cation combines with hydroxide ions in the recovery compartment to produce the desired onium hydroxide. Impurities remain in the feed compartment. Regenerated onium hydroxide is formed and recovered from the recovery compartment 15.

Figure 2:
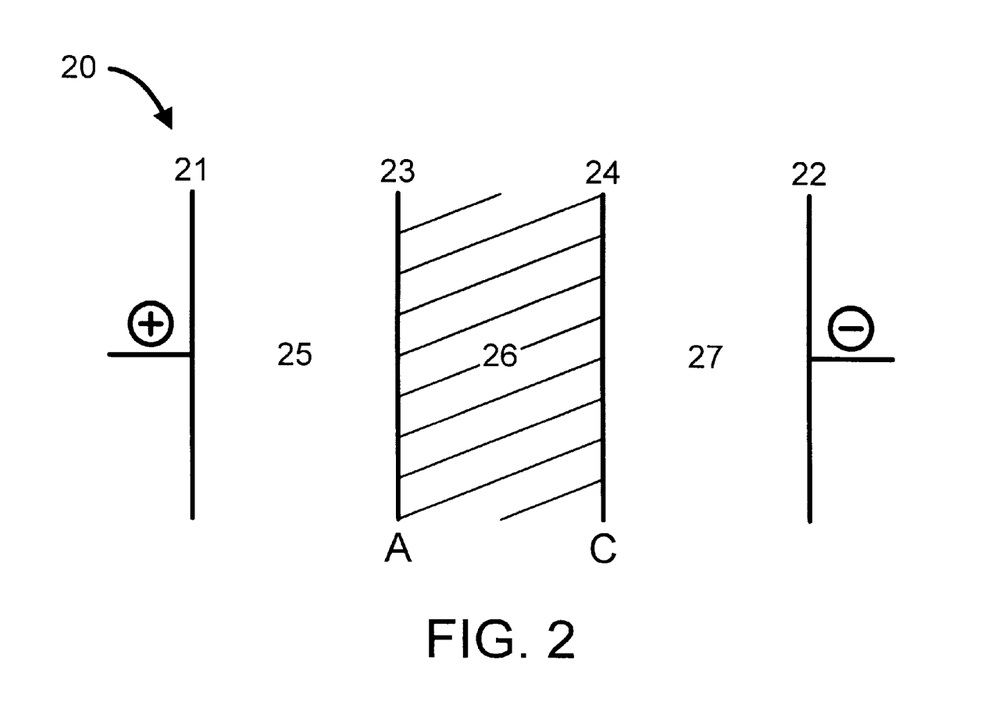
FIG. 2 is a schematic representation of a three compartment electrochemical cell in accordance with the present invention.

Another embodiment of an electrochemical cell is illustrated in FIG. 2, which is a schematic representation of an electrochemical cell 20 containing an anode 21, a cathode 22 and a unit cell containing in sequence beginning at the anode 21, an anion selective membrane 23 and a cation selective membrane 24. The electrochemical cell 20 contains three compartments; namely, an acid compartment 25, a feed compartment 26 and a recovery compartment 27. The feed compartment 26 contains an ion exchange material, which can be a mixed bed resin.

In operation of the electrochemical cell 20 illustrated in FIG. 2, an onium compound is charged to the feed compartment 26. A solution, preferably an aqueous solution, of an ionic compound is charged to the acid compartment 25. An acid solution is charged to the recovery compartment 27.

An electrical potential is established and maintained between the anode and the cathode to produce a flow of current across the cell whereupon the onium compound anion is attracted toward the anode and passes through the anion selective membrane 23 into the acid compartment 25. The onium compound cation is attracted toward the cathode and passes through the ion exchange material and the cation selective membrane 24 into the recovery compartment where it combines with anions from the acid to produce the desired onium salt. Impurities are not attracted to the cathode, pass through the anion selective membrane 23, and/or do not pass through the cation selective membrane 24 and thus remain in the feed compartment 26 and/or migrate to the acid compartment 25. An onium salt containing an anion of choice corresponding to the acid charged to the feed compartment is formed and recovered from the recovery compartment 27. In a preferred embodiment, an acid corresponding to the acid of the onium salt, if any, charged to the feed compartment may be recovered from the acid compartment 25.

In one embodiment, the electrochemical cell 20 illustrated in FIG. 2 is referred to as an electrodeionization cell. When the electrochemical cell 20 is an electrodeionization cell, and the process is conducted in a continuous manner, the process is referred to as continuous deionization.

Figure 3:
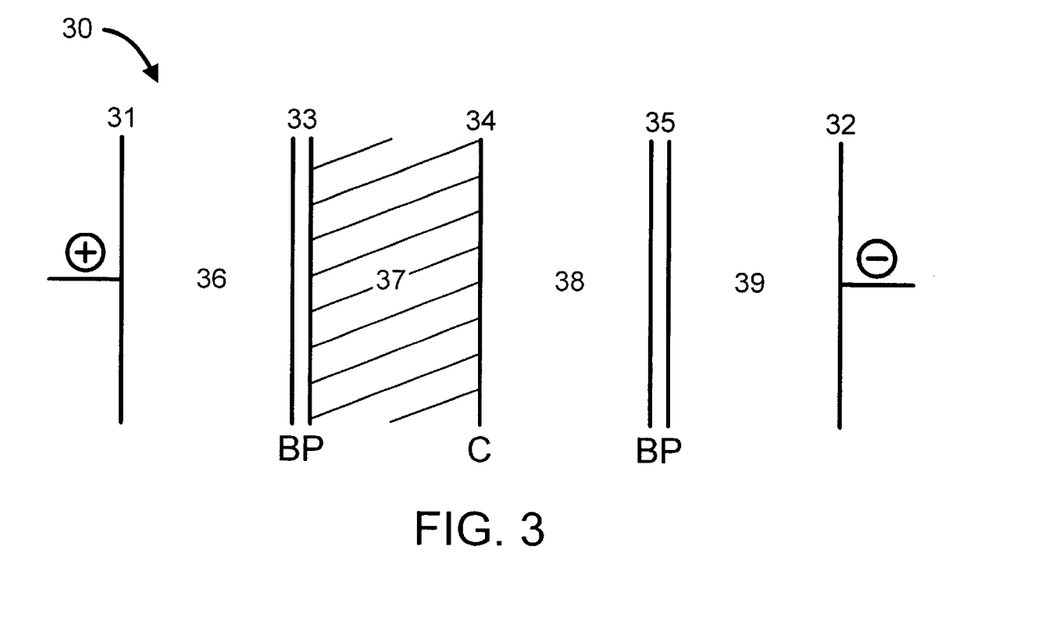
FIG. 3 is a schematic representation of a four compartment electrochemical cell in accordance with the present invention.

Another embodiment of an electrochemical cell is illustrated in FIG. 3, which is a schematic representation of an electrochemical cell 30 containing an anode 31, a cathode 32 and a unit cell containing in sequence beginning at the anode 31, a first bipolar membrane 33, a cation selective membrane 34 and a second bipolar membrane 35. The electrochemical cell 30 contains four compartments; namely, a first buffer compartment 36, an feed compartment 37, a recovery compartment 38 and a second buffer compartment 39. The feed compartment 37 contains an ion exchange material, which can be a cation exchange resin.

In operation of the electrochemical cell 30 illustrated in FIG. 3, an onium compound is charged to the feed compartment 37. A solution, preferably an aqueous solution, of an ionic compound is charged to the recovery compartment 38 and the first and second buffer compartments 36 and 39. An electrical potential is established and maintained between the anode and the cathode to produce a flow of current across the cell whereupon the onium compound cation is attracted toward the cathode and passes through the ion exchange material and the cation selective membrane 34 into the recovery compartment 38 where it combines with hydroxide ions formed on the anode side of the bipolar membrane to produce the desired onium hydroxide. The onium compound anion remains in the feed compartment 37. Impurities remain in the feed compartment 37. Regenerated onium hydroxide is formed and recovered from the recovery compartment 38.

Figure 4A:
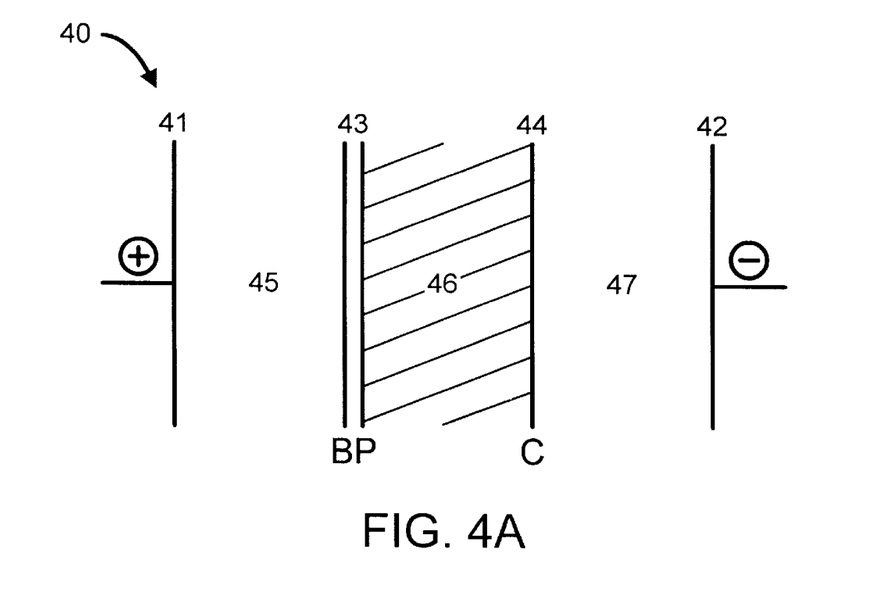
FIG. 4A is a schematic representation of another three compartment electrochemical cell in accordance with the present invention.

Another embodiment of an electrochemical cell is illustrated in FIG. 4A, which is a schematic representation of an electrochemical cell 40 containing an anode 41, a cathode 42 and a unit cell containing in sequence beginning at the anode 41, a bipolar membrane 43 and a cation selective membrane 44. The electrochemical cell 40 contains three compartments; namely, a buffer compartment 45, a feed compartment 46 and a recovery compartment 47. The feed compartment 46 contains an ion exchange material.

In operation of the electrochemical cell 40 illustrated in FIG. 4A, an onium compound is charged to the feed compartment 46. A solution, preferably an aqueous solution, of an ionic compound is charged to the buffer compartment 45 and the recovery compartment 47. An electrical potential is established and maintained between the anode and the cathode to produce a flow of current across the cell whereupon the onium compound anion remains in the feed compartment 46. The onium compound cation is attracted toward the cathode and passes through the ion exchange material and the cation selective membrane 44 into the recovery compartment 47 where it combines with hydroxide ions formed on the surface of the cathode to produce the desired onium hydroxide. Impurities are not attracted to the cathode and/or do not pass through the cation selective membrane 44 and thus remain in the feed compartment 46. Regenerated onium hydroxide is formed and recovered from the recovery compartment 47.

Figure 4B:
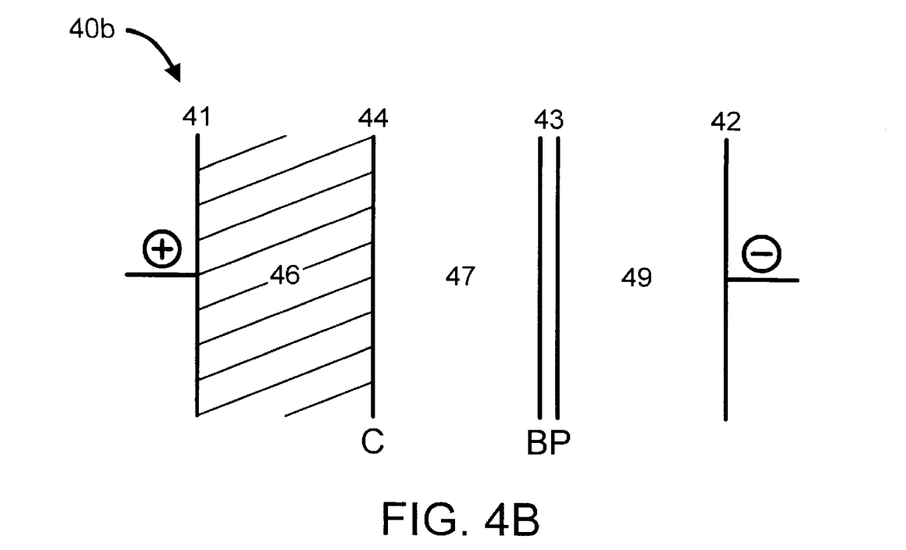
FIG. 4B is a schematic representation of another three compartment electrochemical cell in accordance with the present invention.

Another embodiment of a three compartment electrochemical cell is illustrated in FIG. 4B, which is a schematic representation of an electrochemical cell 40b containing an anode 41, a cathode 42 and a unit cell containing in sequence beginning at the anode 41, a cation selective membrane 44 and a bipolar membrane 43. The electrochemical cell 40b contains three compartments; namely, a feed compartment 46, a recovery compartment 47 and a buffer compartment 49. The feed compartment 46 contains an ion exchange material.

In operation of the electrochemical cell 40b illustrated in FIG. 4B, an onium compound is charged to the feed compartment 46. A solution, preferably an aqueous solution, of an ionic compound is charged to the buffer compartment 49 and the recovery compartment 47. An electrical potential is established and maintained between the anode and the cathode to produce a flow of current across the cell whereupon the onium compound anion remains in the feed compartment 46. The onium compound cation is attracted toward the cathode and passes through the ion exchange material and the cation selective membrane 44 into the recovery compartment 47 where it combines with hydroxide ions formed on the anode side of the bipolar membrane to produce the desired onium hydroxide. Impurities are not attracted to the cathode and/or do not pass through the cation selective membrane 44 and thus remain in the feed compartment 46. Regenerated onium hydroxide is formed and recovered from the recovery compartment 47.

Figure 5:
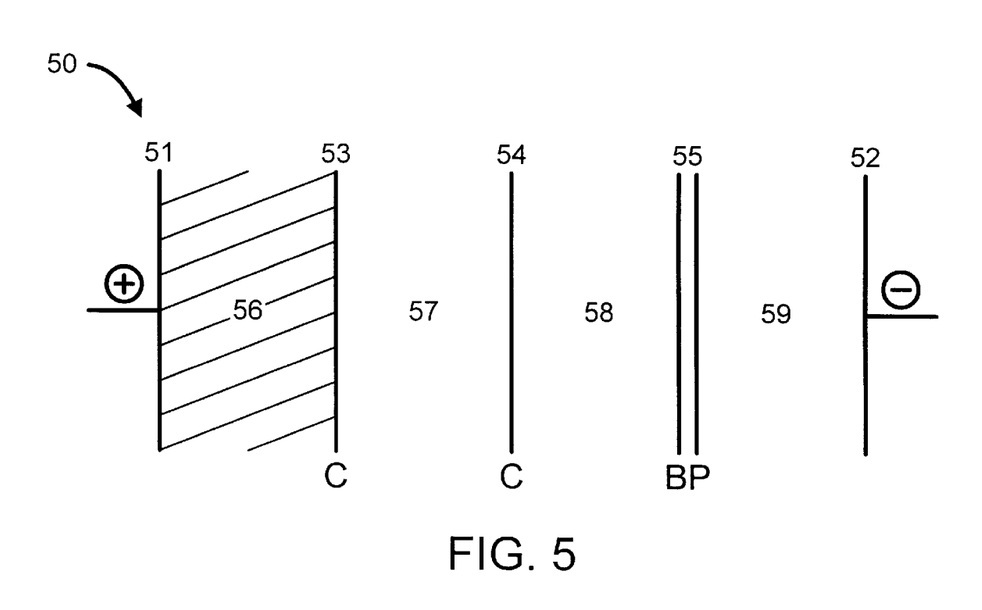
FIG. 5 is a schematic representation of another four compartment electrochemical cell in accordance with the present invention.

Another embodiment of an electrochemical cell is illustrated in FIG. 5, which is a schematic representation of an electrochemical cell 50 containing an anode 51, a cathode 52 and a unit cell containing in sequence beginning at the anode 51, a first cation selective membrane 53, a second cation selective membrane 54, and a bipolar membrane 55. The electrochemical cell 50 contains four compartments; namely, a feed compartment 56, a pass compartment 57, a recovery compartment 58, and a buffer compartment 59. The feed compartment 56 contains an ion exchange material.

In operation of the electrochemical cell 50 illustrated in FIG. 5, an onium compound is charged to the feed compartment 56. A solution, preferably an aqueous solution, of an ionic compound is charged to the pass compartment 57, the buffer compartment 59 and the recovery compartment 58. An electrical potential is established and maintained between the anode and the cathode to produce a flow of current across the cell whereupon the onium compound anion remains in the feed compartment 57. The onium compound cation is attracted toward the cathode and passes through the ion exchange material and the cation selective membranes 53 and 54 and the pass compartment 57 into the recovery compartment 58 where it combines with hydroxide ions formed on the surface of the anode side of the bipolar membrane 55 to produce the desired onium hydroxide. Impurities are not attracted to the cathode and/or do not pass through the cation selective membranes 53 and 54 and thus remain in the feed compartment 56. Regenerated onium hydroxide is formed and recovered from the recovery compartment 58.

Figure 6:
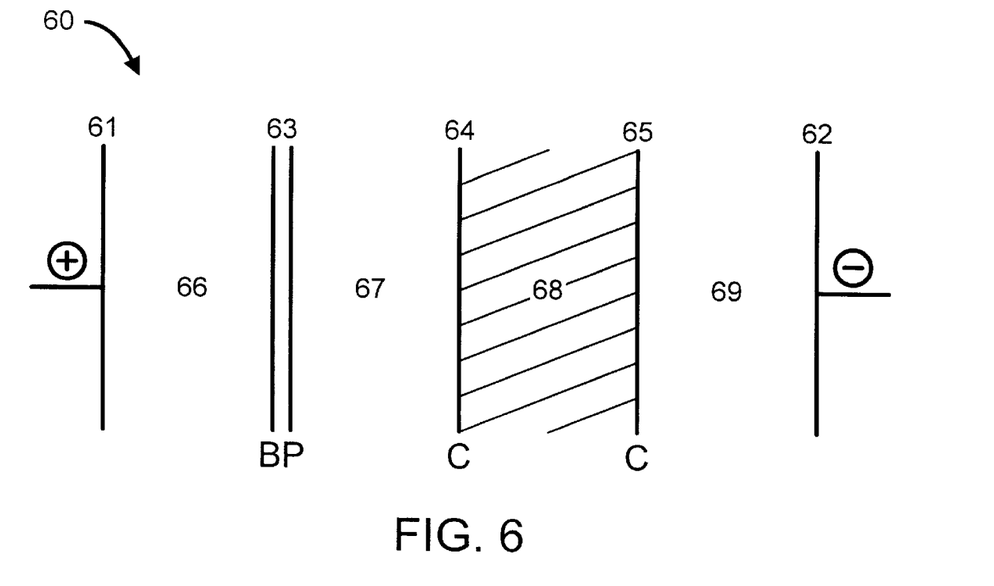
FIG. 6 is a schematic representation of another four compartment electrochemical cell in accordance with the present invention.

Another embodiment of an electrochemical cell is illustrated in FIG. 6, which is a schematic representation of an electrochemical cell 60 containing an anode 61, a cathode 62 and a unit cell containing in sequence beginning at the anode 61, a bipolar membrane 63, a first cation selective membrane 64 and a second cation selective membrane 65. The electrochemical cell 60 contains four compartments; namely, a buffer compartment 66, an acid compartment 67, a feed compartment 68 and a recovery compartment 69. The feed compartment 68 contains an ion exchange material, which can be a mixed bed resin.

In operation of the electrochemical cell 60 illustrated in FIG. 6, an onium compound is charged to the feed compartment 68. A solution, preferably an aqueous solution, of an ionic compound is charged to the buffer compartment 66, the acid compartment 67 and the recovery compartment 69. An electrical potential is established and maintained between the anode and the cathode to produce a flow of current across the cell whereupon the onium compound anion remains in the feed compartment 68. The onium compound cation is attracted toward the cathode and passes through the ion exchange material and the second cation selective membrane 65 into the recovery compartment 69 where it combines with hydroxide ions to produce the desired onium hydroxide. Impurities are not attracted to the cathode and/or do not pass through the cation selective membrane 65 and thus remain in the feed compartment 68 and/or migrate to the acid compartment 67. Regenerated onium hydroxide is formed and recovered from the recovery compartment 69.

Figure 7:
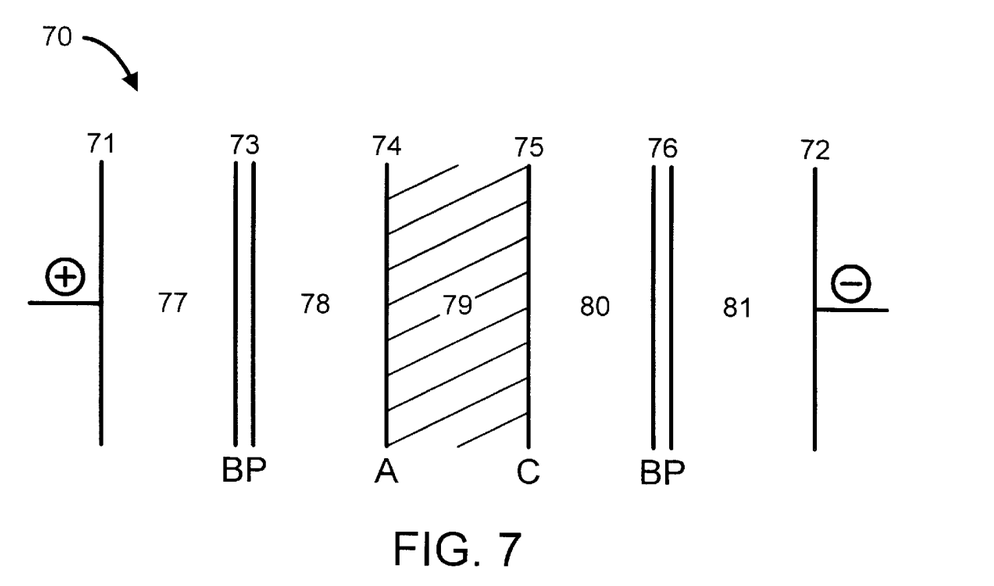
FIG. 7 is a schematic representation of a five compartment electrochemical cell in accordance with the present invention.

Another embodiment of an electrochemical cell is illustrated in FIG. 7, which is a schematic representation of an electrochemical cell 70 containing an anode 71, a cathode 72 and a unit cell containing in sequence beginning at the anode 71, a first bipolar membrane 73, an anion selective membrane 74, a cation selective membrane 75 and a second bipolar membrane 76. The electrochemical cell 70 contains five compartments; namely, a first buffer compartment 77, an acid compartment 78, a feed compartment 79, a recovery compartment 80 and a second buffer compartment 81. The feed compartment 79 contains an ion exchange material.

In operation of the electrochemical cell 70 illustrated in FIG. 7, an onium compound is charged to the feed compartment 79. A solution, preferably an aqueous solution, of an ionic compound is charged to the first and second buffer compartments 77 and 81, the acid compartment 78 and the recovery compartment 80. An electrical potential is established and maintained between the anode and the cathode to produce a flow of current across the cell whereupon the onium compound anion is attracted toward the anode and passes through the anion selective membrane 74 into the acid compartment 78. The onium compound cation is attracted toward the cathode and passes through the ion exchange material and the cation selective membrane 75 into the recovery compartment 80 where it combines with hydroxide ions to produce the desired onium hydroxide. Impurities are not attracted to the cathode, pass through the anion selective membrane 74, and/or do not pass through the cation selective membrane 75 and thus remain in the feed compartment 79 and/or migrate to the acid compartment 78. Regenerated onium hydroxide is formed and recovered from the recovery compartment 80. In a preferred embodiment, acid may be recovered from the acid compartment 78.

Figure 8A:
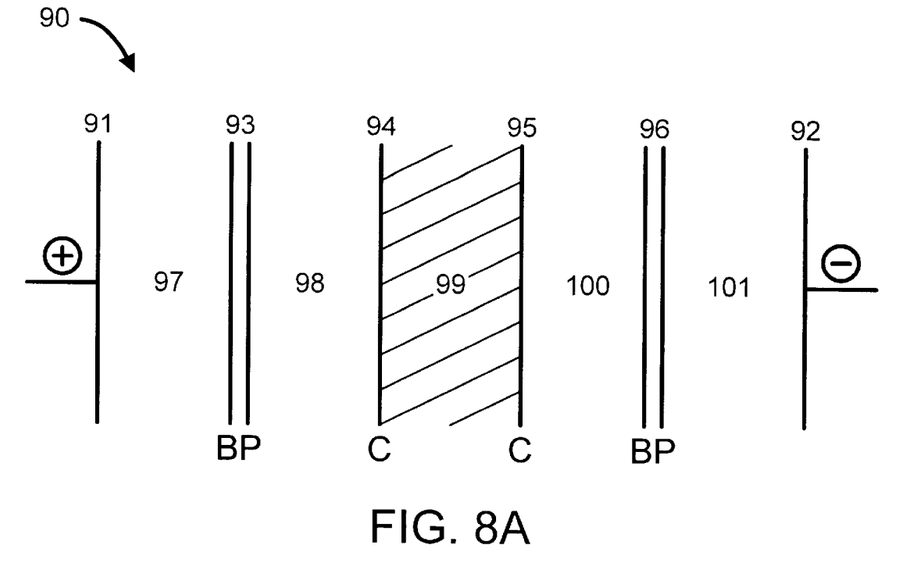
FIG. 8A is a schematic representation of another five compartment electrochemical cell in accordance with the present invention.

Another embodiment of a five compartment electrochemical cell is illustrated in FIG. 8A, which is a schematic representation of an electrochemical cell 90 containing an anode 91, a cathode 92 and a unit cell containing in sequence beginning at the anode 91, a first bipolar membrane 93, a first cation selective membrane 94, a second cation selective membrane 95 and a second bipolar membrane 96. The electrochemical cell 90 contains five compartments; namely, a first buffer compartment 97, an acid compartment 98, a feed compartment 99, a recovery compartment 100 and a second buffer compartment 101. The feed compartment 99 contains an ion exchange material.

Figure 8B:
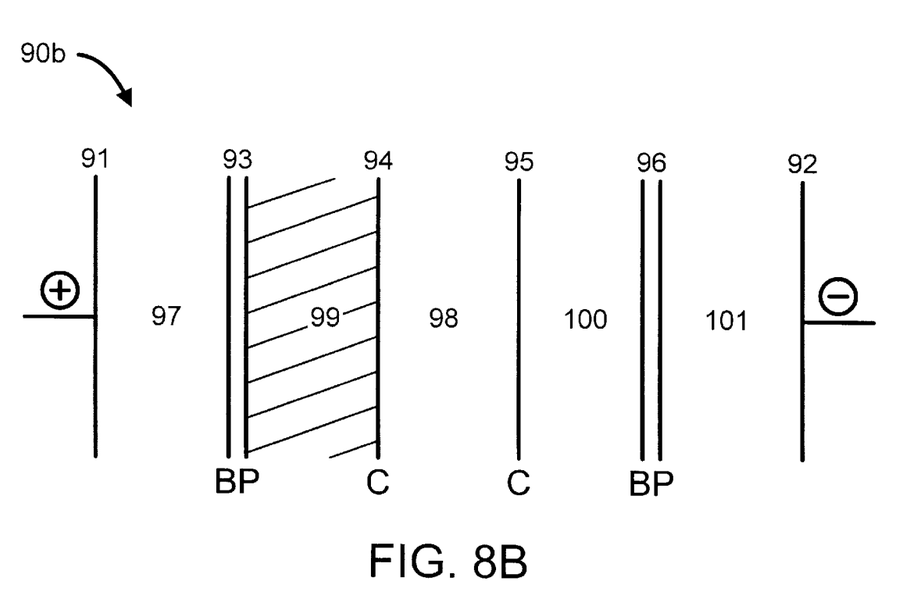
FIG. 8B is a schematic representation of another five compartment electrochemical cell in accordance with the present invention.

Alternatively, an electrochemical cell 90b can contain five compartments in the following order from the anode 91, namely, a first buffer compartment 97, a feed compartment 99, an acid compartment 98, a recovery compartment 100 and a second buffer compartment 101. This embodiment is shown in FIG. 8B and differs from the embodiment illustrated in FIG. 8A in that the acid compartment 98 and the feed compartment 99 have been transposed.

In operation of the electrochemical cell 90 illustrated in FIG. 8A an onium compound is charged to the feed compartment 99. A solution, preferably an aqueous solution, of an ionic compound is charged to the first and second buffer compartments 97 and 101, the acid compartment 98 and the recovery compartment 100. An electrical potential is established and maintained between the anode and the cathode to produce a flow of current across the cell whereupon the onium compound anion remains in the feed compartment 99. The onium compound cation is attracted toward the cathode and passes through the ion exchange material and the second cation selective membrane 95 into the recovery compartment 100 where it combines with hydroxide ions to produce the desired onium hydroxide. Impurities are not attracted to the cathode and/or do not pass through the cation selective membrane 95 and thus remain in the feed compartment 99 and/or migrate to the acid compartment 98. Regenerated onium hydroxide is formed and recovered from the recovery compartment 100.

With regard to the electrochemical cell 90b of FIG. 8B, the operation thereof differs from that of electrochemical cell 90 as follows. After an electrical potential is established and maintained between the anode and the cathode to produce a flow of current across the cell whereupon the onium compound anion remains in the feed compartment 99, the onium compound cation is attracted toward the cathode and passes through the ion exchange material and the first and second cation selective membranes 94 and 95 into the recovery compartment 100 where it combines with hydroxide ions to produce the desired onium hydroxide. Impurities are not attracted to the cathode and/or do not pass through either one of or both of cation selective membranes 94 and 95 and thus remain in the feed compartment 99 and/or migrate to the acid compartment 98. Regenerated onium hydroxide is formed and recovered from the recovery compartment 100.

In some embodiments, gas may accumulate in and/or around the ion exchange resin material. For example, especially in embodiments where the onium compound is an onium salt such as onium bicarbonate and/or onium carbonate, carbon dioxide may accumulate in and/or around the ion exchange resin material. In these instances, the ion exchange resin material may be purged (or the gas may be removed from in and/or around the ion exchange resin material) by at least one of back-washing, fluidizing, and vibration. Thus, the process of the present invention may further include the step of at least one of back-washing, fluidizing, and vibrating the electrochemical ion exchange cell.

Although not wishing to be bound by any theory, operation of the electrochemical cells according to the invention is believed to be based, in part, on the migration of the cation and/or anion of the onium salt, initially charged in the feed compartment, through the ion exchange material to the recovery or acid compartment as a result of the current applied.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fail within the scope of the appended claims.

What is claimed is:

1. A process for recovering one of an onium hydroxide and an onium salt from a solution containing an onium compound, comprising:
   (A) charging the solution containing the onium compound to an electrochemical cell comprising at least two compartments, a cathode, an anode, and a divider, wherein at least one compartment comprises an ion exchange material;
   (B) passing a current through the electrochemical cell whereby the onium hydroxide or the onium salt is produced; and
   (C) recovering the onium hydroxide or the onium salt from the electrochemical cell.

2. The process of claim 1, wherein the ion exchange material comprises at least one of a cation exchange resin and an anion exchange resin.

3. The process of claim 1, wherein the ion exchange material comprises at least one of a weakly acidic cation exchange resin, an intermediately acidic cation exchange resin, a chelating cation exchange resin and a strongly acidic cation exchange resin.

4. The process of claim 1, wherein the ion exchange material is in the form of at least one of powder, pellets, granuoles, films, and fibrous materials.

5. The process of claim 1, wherein the compartment comprising the ion exchange material comprises at least about 10% by volume of the ion exchange material.

6. The process of claim 1, wherein the ion exchange material comprises a crown ether compound.

7. The process of claim 1, wherein the divider is a cation selective membrane and wherein the solution containing the onium compound is charged to a feed compartment formed adjacent and on the anode side of the cation selective membrane, and the onium hydroxide or the onium salt is recovered from a recovery compartment formed adjacent and on the cathode side of the cation selective membrane, wherein the feed compartment comprises the ion exchange material.

8. The process of claim 1, wherein the electrochemical cell comprises at least three compartments, a cathode, an anode, and in order from the anode to the cathode, a bipolar membrane and a cation selective membrane, the solution containing the onium compound is charged to a feed compartment formed by the bipolar membrane and the cation selective mem- brane, and the onium hydroxide or the onium salt is recovered from a recovery compartment formed adjacent and on the cathode side of the cation selective membrane, wherein the feed compartment comprises the ion exchange material.

9. The process of claim 1, wherein the electrochemical cell comprises at least three compartments, a cathode, an anode, and in order from the anode to the cathode, an anion selective membrane and a cation selective membrane, the solution containing the onium compound is charged to a feed compartment formed by the anion selective membrane and the cation selective membrane, and the onium hydroxide or the onium salt is recovered from a recovery compartment formed adjacent and on the cathode side of the cation selective membrane, wherein the feed compartment comprises the ion exchange material.

10. The process of claim 9, wherein the electrochemical cell is an electrodeionization cell and the process is continuous deionization.

11. The process of claim 1, wherein the electrochemical cell comprises at least three compartments, a cathode, an anode, and in order from the anode to the cathode, a first cation selective membrane and a second cation selective membrane, the solution containing the onium compound is charged to a feed compartment formed by either the first and second cation selective membranes or adjacent and on the anode side of the first cation selective membrane, and the onium hydroxide or the onium salt is recovered from a recovery compartment formed adjacent and on the cathode side of the second cation selective membrane, wherein the feed compartment comprises the ion exchange material.

12. The process of claim 1, wherein the electrochemical cell comprises at least three compartments, a cathode, an anode, and in order from the anode to the cathode, a cation selective membrane and a bipolar membrane, the solution containing the onium compound is charged to a feed compartment formed adjacent and on the anode side of the cation selective membrane, and the onium hydroxide or the onium salt is recovered from a recovery compartment formed by the bipolar membrane and the cation selective membrane, wherein the feed compartment comprises the ion exchange material.

13. The process of claim 1, wherein the onium hydroxide comprises a quaternary ammonium hydroxide represented by the formula wherein $R^1$, $R^2$, $R^3$ and $R^4$ are each independently alkyl groups containing from 1 to about 10 carbon atoms, aryl groups, or $R^1$ and $R^2$ are alkyl groups which together with the nitrogen atom may form an aromatic or non-aromatic heterocyclic ring provided that if the heterocyclic group contains a—C=N—, $R^3$ is the second bond.

14. The process of claim 1, wherein the solution containing the onium compound further contains impurities, the process further comprising pretreating the solution containing the onium compound and impurities prior to performing step (A) to remove at least a portion of the impurities.

15. The process of claim 14, wherein pretreating involves at least one of evaporation, contact with a metal complexing compound, nanofiltration, ultrafiltration, adsorption, precipitation, co-precipitation, neutralization, chemical oxidation, electrochemical oxidation, distillation, and reverse osmosis.

16. The process of claim 1, wherein the onium compound recovered in step (C) contains impurities, the process further comprising post-treating the onium compound and impurities to remove at least a portion of the impurities.

17. The process of claim 16, wherein post-treating involves at least one of evaporation, contact with a metal complexing compound, nanofiltration, ultrafiltration, adsorption, precipitation, co-precipitation, neutralization, chemical oxidation, electrochemical oxidation, distillation, and reverse osmosis.

18. A process for recovering one of an onium hydroxide and an onium salt from a solution containing an onium compound, comprising:
  (A) charging the solution containing the onium compound to an electrochemical cell comprising at least two compartments, a cathode, an anode, and a cation selective membrane, wherein at least one compartment comprises a cation exchange material;
  (B) passing a current through the electrochemical cell whereby the onium hydroxide or the onium salt is produced; and
  (C) recovering the onium hydroxide or the onium salt from the electrochemical cell.

19. The process of claim 18, wherein the cation exchange material comprises at least one of a weakly acidic cation exchange resin, an intermediately acidic cation exchange resin and a strongly acidic cation exchange resin.

20. The process of claim 18, wherein the cation exchange material comprises a strongly acidic cation exchange resin.

21. The process of claim 18, wherein the cation exchange material comprises a selective cation exchange resin.

22. The process of claim 18, wherein the compartment comprising the cation exchange material comprises at least about 5% by volume of the cation exchange material.

23. The process of claim 18, wherein the electrochemical cell further comprises at least one bipolar membrane.

24. The process of claim 18, wherein the electrochemical cell further comprises at least one anion selective membrane.

25. The process of claim 18, wherein the electrochemical cell comprises at least five compartments, a cathode, an anode, and in order from the anode to the cathode, a first bipolar membrane, an anion selective membrane, a cation selective membrane, and a second bipolar membrane, the solution containing the onium compound is charged to a feed compartment formed by the anion selective membrane and the cation selective membrane, and the onium hydroxide or the onium salt is recovered from a recovery compartment formed by the cation selective membrane and the second bipolar membrane, wherein the feed compartment comprises the cation exchange material.

26. The process of claim 18, wherein the electrochemical cell comprises at least five compartments, a cathode, an anode, and in order from the anode to the cathode, a first bipolar membrane, a first cation selective membrane, a second cation selective membrane, a second bipolar membrane, the solution containing the onium compound is charged to a feed compartment formed by either the first and second cation selective membranes or the first bipolar membrane and the first cation selective membrane, and the onium hydroxide or the onium salt is recovered from a recovery compartment formed by the second cation selective membrane and the second bipolar membrane, wherein the feed compartment comprises the cation exchange material.

27. The process of claim 18, wherein the solution containing the onium compound further contains impurities, the process further comprising pretreating the solution containing the onium compound and impurities prior to performing step (A) to remove at least a portion of the impurities.

28. The process of claim 18, wherein the onium compound recovered in step (C) contains impurities, the process further comprising post-treating the onium compound and impurities to remove at least a portion of the impurities.

29. A process for recovering a quaternary ammonium hydroxide from a solution containing a quaternary ammonium compound, comprising:
  (A) charging the solution containing the quaternary ammonium compound to an electrochemical cell comprising at least two compartments, a cathode, an anode, and a cation selective membrane, wherein at least one compartment comprises an ion exchange material;
  (B) passing a current through the electrochemical cell whereby the quaternary ammonium hydroxide is regenerated; and
  (C) recovering the quaternary ammonium hydroxide from the electrochemical cell.

30. The process of claim 29, wherein the quaternary ammonium hydroxide comprises at least one of tetramethylammonium hydroxide, tetraethylammonium hydroxide, tetrapropylammonium hydroxide, tetrabutylammonium hydroxide, methyltriethylammonium hydroxide, methyltributylammonium hydroxide, methyltripropylammonium hydroxide, and diethyldimethylammonium hydroxide.

31. The process of claim 29, wherein the ion exchange material comprises at least one of a cation exchange resin and an anion exchange resin.

32. The process of claim 29, wherein the ion exchange material comprises at least one of a weakly acidic cation exchange resin, an intermediately acidic cation exchange resin and a strongly acidic cation exchange resin.

33. The process of claim 29, wherein the ion exchange material is in the form of at least one of powder, pellets, granuoles, films, and fibrous materials.

34. The process of claim 29, wherein the solution containing the quaternary ammonium compound is charged to a feed compartment formed adjacent and on the anode side of the cation selective membrane, and the quaternary ammonium hydroxide is recovered from a recovery compartment formed adjacent and on the cathode side of the cation selective membrane, wherein the feed compartment comprises the ion exchange material.

35. The process of claim 29, wherein the electrochemical cell comprises at least three compartments, a cathode, an anode, and in order from the anode to the cathode, a bipolar membrane and a cation selective membrane, the solution containing the quaternary ammonium compound is charged to a feed compartment formed by the bipolar membrane and the cation selective membrane, and the quaternary ammonium hydroxide is recovered from a recovery compartment formed adjacent and on the cathode side of the cation selective membrane, wherein the feed compartment comprises the ion exchange material.

36. The process of claim 29, wherein the electrochemical cell comprises at least three compartments, a cathode, an anode, and in order from the anode to the cathode, an anion selective membrane and a cation selective membrane, the solution containing the quaternary ammonium compound is charged to a feed compartment formed by the anion selective membrane and the cation selective membrane, and the quaternary ammonium hydroxide is recovered from a recovery compartment formed adjacent and on the cathode side of the cation selective membrane, wherein the feed compartment comprises the ion exchange material.

37. The process of claim 29, wherein the solution containing the quaternary ammonium compound further contains impurities, the process further comprising pretreating the solution containing the quaternary ammonium compound and impurities prior to performing step (A) to remove at least a portion of the impurities.

38. The process of claim 29, wherein the quaternary ammonium compound recovered in step (C) contains impurities, the process further comprising post-treating the quaternary ammonium compound and impurities to remove at least a portion of the impurities.

* * * * *